United States Patent [19]

Kondo et al.

[11] 4,166,064

[45] Aug. 28, 1979

[54] PROCESS FOR PREPARING HIGH CIS 3-(2,2,2-TRICHLOROETHYL)-2,2-DIMETHYLCYCLOPROPANE-1-CARBOXYLATES

[75] Inventors: Kiyoshi Kondo; Akira Negishi, both of Yamato; Kikuo Sugimoto, Fujino, all of Japan

[73] Assignee: FMC Corporation, Philadelphia, Pa.

[21] Appl. No.: 877,151

[22] Filed: Feb. 13, 1978

[51] Int. Cl.$^2$ ..................... C07C 61/04; C07D 307/54
[52] U.S. Cl. ............................. 260/347.4; 260/326 A; 260/340.5 R; 260/347.2; 260/465 D; 560/124; 549/76; 549/77; 549/79; 549/60; 549/65; 549/66
[58] Field of Search ................... 560/124; 260/326 A, 260/332.2 R, 340.5 R, 347.2, 347.4, 465 D

[56] References Cited
U.S. PATENT DOCUMENTS 3,077,496  2/1963  Julia ................................. 560/124 X

FOREIGN PATENT DOCUMENTS 833278  10/1976  Belgium .
2605398  8/1976  Fed. Rep. of Germany .
49-122242  10/1974  Japan .

OTHER PUBLICATIONS

Kondo et al., Synthetic Pyrethroids, ACS Symposium Series, No. 42, (1977), Chapter 12.
Itaya et al., Synthetic Pyrethroids, ACS Symposium Series No. 42, (1977), Chapter 4.

*Primary Examiner*—Richard Raymond
*Attorney, Agent, or Firm*—Robert M. Kennedy; H. R. Ertelt

[57] ABSTRACT

A process is described whereby esters of 3-(2,2,2-trichloroethyl)-2,2-dimethylcyclopropane-1-carboxylic acid are prepared predominantly in their cis isomer form. The process comprises treating a 4,6,6,6-tetrachloro-3,3-dimethylhexanoate with an alkali metal tert-alkoxide under controlled conditions of temperature in the presence of a defined solvent-cosolvent mixture. The products of the process are intermediates in the production of pyrethroid insecticides.

7 Claims, No Drawings

PROCESS FOR PREPARING HIGH CIS 3-(2,2,2-TRICHLOROETHYL)-2,2-DIMETHYLCYCLOPROPANE-1-CARBOXYLATES

BACKGROUND OF THE INVENTION

1. Field of the Invention

This invention pertains to processes for preparing dihaloethenylcyclopropanecarboxylate insecticides, more specifically to a process for preparing a 3-(2,2,2-trichloroethyl)-2,2-dimethylcyclopropane-1-carboxylate predominantly in its cis isomer form as an intermediate in the production of dichloroethenylcyclopropanecarboxylate insecticides predominantly in their cis isomer form.

2. Description of the Prior Art

Belgian Pat. No. 833,278 describes a process for making dihaloethenylcyclopropanecarboxylates. The patent discloses, inter alia, that the base induced dehydrohalogenation of certain 4,6,6,6-tetrahalohexanoates can be controlled by varying the reaction conditions to give any one of four different products including a trihaloethylcyclopropanecarboxylate and a dihaloethenylcyclopropanecarboxylate exemplified respectively by compounds Z and C below wherein R is a defined alcohol residue.

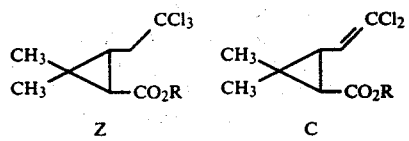

Under certain conditions compound Z is an intermediate in the reaction leading to compound C. These two compounds correspond to compounds Z and C described in the instant application, and differ from them mainly in the relative amounts of cis and trans isomers in each. The process of the Belgian patent reportedly produces compound C and, presumably, the compound Z intermediate, wherein the trans isomer comprises from 50% to 90% of the isomer mixture. The process of the present application produces compounds Z and C wherein the cis isomer comprises more than 50% of the isomer mixture.

To obtain compound C by the process of the Belgian patent, a 4,6,6,6-tetrahalohexanoate is allowed to react with at least 1.5 molar equivalent of base (sodium and potassium hydroxide, alkali metal alkoxides, sodium hydride, and sodium napthalide are disclosed) in a solvent (alcohols and ethers are disclosed) at a temperature of from −30° C. to 200° C. When the reaction is conducted at 25° C. to 50° C. in the presence of sodium or potassium tert-butoxide in benzene, dioxane, dimethylformamide, tetrahydrofuran, tert-butyl alcohol, or a mixture of tert-butyl alcohol with benzene, the product is reported to be compound Z. Compound Z can be converted to compound C by further treatment with base.

It was reported in the Belgian patent that the ratio of cis to trans isomers in the product compound C was, to a certain extent, a function of the reaction temperature, with the trans isomer being favored at higher temperatures. In no case, however, was the cis isomer reported to be produced in excess of the trans, even at low tempertures. The highest cis/trans ratio disclosed for compound C is 1:1. In that case, ethyl 4,6,6,6-tetrachlorohexanoate was treated at 0° C. for two hours with 2.2 equivalents of sodium tert-butoxide in tetrahydrofuran to give the 50/50 mixture of cis and trans isomers of ethyl 3-(2,2-dichloroethenyl)-2,2-dimethylcyclopropane-1-carboxylate.

Similarly, Japanese Patent Application No. 122242/74 (OPI No. 59839/76) discloses a process for preparing either compound Z or compound C above. There R is defined as hydrogen or lower alkyl. According to the Japanese application when a 4,6,6,6-tetrachlorohexanoate is treated with a base at from 0° C. to 25° or 30° C. for up to one or two hours the product is compound Z. To prepare compound C, the reaction is conducted at a higher temperature and for a longer period of time. The process is disclosed as producing exclusively the trans isomer. Suitable bases include various alkyl lithium compounds and alkali metal alkoxides, amides, and hydroxides. The type of solvent used is reported not to be critical; alcohols, ethers, aromatic hydrocarbons, and liquid ammonia are disclosed. Aromatic hydrocarbons are said to be generally used.

German Offenlegungsschrift No. 2605398 discloses generically, inter alia, the process exemplified by the following chemical equations.

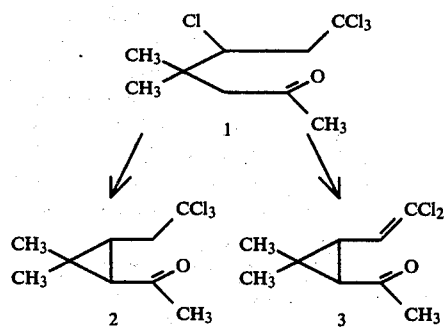

According to the disclosure, the dehydrochlorination of the tetrachloro ketone 1 is effected by treatment with base (alkali metal hydroxides and alkoxides are disclosed) at from −20° to 120° C. in a suitable solvent (water, water plus an alcohol, alcohols, ethers, and aromatic hydrocarbons are disclosed). The nature of the product and its isomer makeup are reported to depend upon the reaction temperature and other reaction conditions such as the nature of the base used. Generally, when the reaction is conducted in a lower alcohol at from −20° to 25° C. the product is compound 2 wherein the cis isomer predominates. At higher temperatures the trans isomer predominates and the product is compound 2 and/or compound 3. Depending upon the reaction conditions it is reported that one can obtain product having a cis/trans ratio of from 1:9 to 9:1. Although this process pertains to dehydrochlorinations involving ketones rather than carboxylic acid esters as in the Belgian and Japanese references above, the teaching that the cis/trans isomer ratio in the product is temperature dependent is consistent with the Belgian disclosure. The process is further described and expanded in *Synthetic Pyrethroids*, ACS Symposium Series, No. 42, M. Elliott, Ed., American Chemical Society, Washington, D.C., 1977, chapter 4. Compound 2 is described as being a key intermediate for the preparation of the acid corresponding to compound C having a controlled cis/trans isomer ratio.

The foregoing prior art teaches or suggests that temperature and base are the critical factors in determining the cis/trans distribution when a 4,6,6,6-tetrachlorohexanoate is converted by dehydrohalogenation to either compound Z or compound C.

It has now been found that in systems employing an alkali metal tert-alkoxide as the base, for any given temperature up to about 30° C., the ratio of cis to trans isomers in the product, compound Z or compound C, is unexpectedly and surprisingly increased by employing a solvent system comprising a non-polar or slightly polar solvent and a selected polar aprotic cosolvent. Moreover, it has been determined that the cis/trans ratio in the intermediate, compound Z, will generally control the cis/trans ratio in compound C when the latter is prepared via compound Z in accordance with prior art methods.

SUMMARY OF THE INVENTION

Consistent with these findings the present invention comprises dehydrochlorinating a 4,6,6,6-tetrachloro-3,3-dimethylhexanoate to form the corresponding 3-(2,2,2-trichloroethyl)-2,2-dimethylcyclopropane-1-carboxylate predominantly in its cis isomer form, by conducting the reaction in a solvent-cosolvent mixture wherein the co-solvent is a dipolar aprotic solvent, at a temperature of up to about 30° C. in the presence of an alkali metal tert-alkoxide base. The word "predominantly" as used herein means comprising greater than 50% of the isomer mixture of the desired product. The terms "high cis" and "cis rich" mean the cis isomer comprises more than 50% of the isomer mixture of the desired product. The word "lower" when used herein to modify "alkyl" means alkyl of 1 to 4 carbon atoms.

DETAILED DESCRIPTION OF THE INVENTION

The process of this invention comprises treating a compound of formula (B)

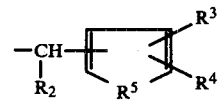

wherein R is defined as below, with an alkali metal tert-alkoxide, preferably having 4 to 6 carbon atoms, at a temperature of about −80° to about 30° C. in the presence of a solvent system comprising (a) a solvent selected from (1) an aliphatic hydrocarbon of 5 to 8 carbon atoms, (2) an aromatic unsubstituted hydrocarbon having 6 ring carbon atoms, or substituted with 1 to 3 substituents selected from alkyl of 1 or 2 carbon atoms and chlorine, (3) a tertiary alcohol of 4 to 6 carbon atoms, (4) an ether selected from diethyl ether, 1,2-dimethoxyethane, 2-methoxyethyl ether, tetrahydrofuran, and dioxane, and (5) a mixture of any of these solvents, and (b) a dipolar aprotic cosolvent selected from (1) hexamethylphosphoramide, (2) dimethylformamide, (3) dimethylacetamide, (4) dimethylsulfoxide, and (5) N-methylpyrrolidone, the ratio of solvent to cosolvent being from about 20:1 to about 2:1 by volume, to give a high cis compound of formula (Z)

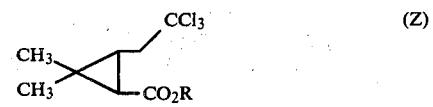

wherein R is defined as below.

Treatment of high cis compound Z with base produces a high cis compound of formula C.

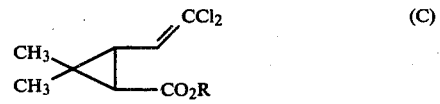

wherein R is defined as below.

In the formulas above, R is lower alkyl or a group $R^1$ which is allethrolonyl, tetrahydrophthalimidomethyl, or is represented by the formula

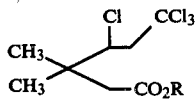

in which $R^2$ is hydrogen, lower alkyl, lower alkynyl, trihalomethyl, or cyano, $R^3$ and $R^4$ are independently hydrogen, lower alkyl, lower alkenyl, phenyl, benzyl, phenoxy, phenylthio or are joined to form a methylenedioxy group attached to two adjacent ring carbon atoms of a phenyl ring, and $R^5$ is divalent oxygen or sulfur or vinylene. Frequently R will be alkyl of 1 to 4 carbon atoms, preferably of 1 or 2 carbon atoms. When R is $R^1$, $R^1$ is preferably 3-phenoxybenzyl, α-cyano-3-phenoxybenzyl or 5-benzyl-3-furylmethyl.

The high cis compounds of formula C above wherein R is $R^1$, for which the compounds of formula Z are intermediates, are highly active insecticides. The importance of the process of this invention is underscored by the fact that cis pyrethroids are known to be generally more toxic to insects than are the corresponding trans pyrethroids. (M. Elliott, Ed., *Synthetic Pyrethroids*, ACS Symposium Series, No. 42, American Chemical Society, Washington, D.C., 1977, p. 53.)

Suitable alkali metal tert-alkoxide bases useful in the process of this invention include the sodium or potassium salts of tert-butyl alcohol or tert-amyl alcohol. The preferred base is sodium tert-butoxide. For best results the base should be freshly prepared just prior to use or prepared in situ. These bases are generally used in an amount in excess of 1 mol equivalent, preferably 1 to 2 mol equivalents, based on compound B.

A variety of types of solvents are suitable for use in the present process and the choice from among them is not critical so long as the solvent is employed in combination with one of the above defined cosolvents. Suitable solvents include various aliphatic hydrocarbons such as pentane, hexane, heptane, and octane, either straight or branched chain; aromatic hydrocarbons such as benzene, toluene, xylene, chlorobenzene, and the like; tertiary alcohols such as tert-butyl alcohol and tert-amyl alcohol; and ethers such as diethyl ether, 1,2-dimethoxyethane, 2-methoxyethyl ether, tetrahydrofuran, and dioxane. Mixtures of any of the above solvents are also appropriate, and may be advantageously used in many cases to aid in dissolution of the base.

Preferred cosolvents are dimethylacetamide, dimethylformamide, and, particularly, hexamethylphosphoramide. Although the cosolvent may be effectively used over a wide concentration range with respect to the solvent, it is usually employed as the minor component in the range of about, 3:1 to about 10:1, preferably 4:1 to 6:1 by volume. Preferred solvent-cosolvent combinations include the following:

| | |
|---|---|
| hexane - hexamethylphosphoramide | (5:1) |
| hexane - dimethylacetamide | (5:1) |
| hexane - dimethylformamide | (5:1) |
| toluene -hexamethylphosphoramide | (10:1) |
| t-butanol - hexamethylphosphoramide | (5:1) |
| t-butanol - hexane-hexamethylphosphoramide | (5:1:1) |
| t-butanol-hexane-diemthylacetamide | (5:1:1) |

While the critical feature of this invention resides in the use of a defined cosolvent, the effectiveness of the process depends also on other parameters such as the reaction temperature and the nature of the base used. The use of a strong hydrogen-abstracting base such an alkali metal tertiary alkoxide is essential for the selective preparation of compound Z from compound B. The formation of the cis isomer in the resulting compound Z is favored at lower temperatures. However, the solubility of the base in a suitable solvent, and thus the rate of reaction, decrease proportionately with a decrease in temperature. This problem is circumvented by the cosolvent which aids in the dissolution of the base and allows the reaction to be conducted at a temperature that would otherwise be unfeasible. The cosolvent may also facilitate the reaction by strengthening the nucleophilicity of the carbanion produced as a result of the base abstraction of a hydrogen atom from compound B. While the use of a cosolvent is essential to the process, the use of excess cosolvent is to be avoided. As the solvent to cosolvent ratio decreases from about 5:1 product selectivity decreases and in addition to compound Z one gets increasing amounts of a 4,6,6-trichloro-3,3-dimethyl-5-hexenoate and a 6,6,6-trichloro-3,3-dimethyl-4-hexenoate.

The temperature range over which the process is operative is from about −80° to about 30° C., advantageously from about −60° to about 10° C. It is preferably conducted at about −25° to about 10° C. Reaction temperatures higher than about 10° C. are generally employed only after an initial reaction period of up to about 12 hours at a much lower temperature, usually below about −25° C. For example, when the reaction is conducted at about −60° C., a major portion of the starting material, compound B, will have been converted into cis rich compound Z within about 12 hours. To assure complete conversion it is convenient to allow the reaction mixture to stand, with stirring if heterogeneous, at room temperature for up to an additional 24 hours. This is usually not necessary if the reaction is conducted in the range of −25° to 10° C.

The product of the process of this invention, high cis compound Z, can be converted in one or more steps to insecticidally active high cis compound C wherein R is $R^1$ by methods generally within the skill of the art. One is limited, however, in the choice of conditions to those that do not cause isomerization of the cis to trans isomer in either compound Z or the product, compound C. Under the conditions described below compound Z can be effectively dehydrochlorinated to compound C without isomerization. Where compound C is an intermediate, i.e., where $R \neq R^1$, it can generally be converted to the desired insecticidally active compound without isomerization by ester exchange with $R^1$-OH or by mild hydrolysis and reesterification with $R^1$-OH by the usual methods for conducting this type of reaction.

In contrast to the limited number of bases that are acceptable for use in preparing high cis compound Z by the process of this invention, a wide variety of types of bases are capable of and suitable for effecting the dehydrochlorination of high cis compound Z to give high cis compound C. These include alkali metal alkoxides, alkali metal amides, and strong amine bases such as 1,5-diazabicyclo[4.3.0]non-5-ene (DBN), 1,5-diazabicyclo-[5.4.0]undec-5-ene (DBU), 1,4-diazabicyclo[2.2.-2]octane (DABCO), piperidine, and pyrrolidine. Although alkali metal hydroxides may also be used, the product is the acid of high cis compound C rather than an ester. However, if the conditions are sufficient to cause ester hydrolysis but are too mild to effect dehydrohalogenation, the product will be the acid of high cis compound Z.

Solvents suitable for use in the conversion of compound Z to compound C are preferably aprotic in nature with the exception that water, lower alcohols, or aqueous-alcoholic mixtures are employed when the base is an alkali metal hydroxide. The alkali metal alkoxide bases may be advantageously used with hydrocarbon solvents such as n-octane, although mixtures of hydrocarbon solvents with lower alcohols may also be acceptable. For example, use of sodium methoxide in n-octane, or in a mixture of n-octane and methanol under conditions allowing for the azeotropic removal of the methanol during the course of the reaction, gives results far superior to those obtained when sodium methoxide is used in methanol only. Polar aprotic solvents having a boiling point higher than 80° C. such as dimethylformamide or dimethylacetamide are generally used with the strong amine bases, while ether solvents such as tetrahydrofuran are used more frequently with alkali metal amides.

When the solvent is a hydrocarbon or an ether it is preferably employed in combination with a dipolar aprotic cosolvent. The cosolvents described above for use in the preparation of high cis compound Z are suitable for use here.

The conditions of temperature and reaction time will generally vary with the nature of the base and the solvent system used. Specific examples are shown in the following table.

| Base | Solvent System | Temperature/ Time |
|---|---|---|
| Sodium hydroxide | Water | 100°/15 hours |
| Sodium methoxide | hexane/hexamethylphoshoramide (5:1) | 25°/1-3 hours |
| Sodium methoxide | octane/dimethylacetamide (5:1) | 25°/3 hrs/100 mm Hg |
| DBU | dimethylformamide | 100°/1-3 hours |
| Piperidine | dimethylformamide | 100°/24 hours |
| Sodium amide | tetrahydrofuran | 40°/19 hours |

The tabulation above is included merely to serve as guide and to point out certain reaction conditions that have been found to effect satisfactorily the conversion of high cis compound Z to high cis compound C. Numerous other conditions will, of course, also be satisfactory.

It is also possible to prepare compound C directly from compound B, without isolation of compound Z. This can be accomplished either by adding sufficient tertiary alkoxide base at the outset for both reactions, or by adding a suitable base for the second dehydrochlorination after the first has gone to completion. The latter method is generally preferred. The conditions described above for the conversion of compound Z to compound C are generally applicable here, even though compound Z is not isolated. However, since a dipolar aprotic cosolvent will already be present in the reaction mixture containing compound Z, additional cosolvent need not be added. Alkali metal hydroxides are also suitable for use here to give directly the acid of high cis compound C.

The present invention is further illustrated in greater detail by the following Examples. Temperatures are in degrees centigrade. Product distribution was determined by gas liquid phase chromatography (glpc) from the ratios of peak areas. Acenaphthene was used as an internal standard. The glpc instrument used was a Hitachi Model 163 (FID). Unless otherwise specified, concentration of liquid volume was carried out under the reduced pressure produced by a water aspirator.

The following examples illustrate the effect of cosolvent on the cis/trans ratio and product distribution in the conversion of compound B to compound Z by the process of the invention.

EXAMPLE I

| (a) | Compound B: | Ethyl 4,6,6,6-tetrachloro-3,3-dimethyl-hexanoate |
|---|---|---|
| | Scale | 5 mmol |
| | Base | Sodium tert-butoxide (9.4 mmol) |
| | Solvent | Hexane |
| | Cosolvent | None |
| | Procedure | |

Sodium tert-butoxide (0.9 g, 9.4 mmol) was added in solid form to ethyl 4,6,6,6-tetrachloro-3,3-dimethylhexanoate (1.55 g, 5 mmol) in 5 ml of n-hexane. The reaction was conducted at −26° C. for 6 hours then at −5° to 0° C. for 45 hours. Analysis of the reaction mixture by glpc showed the following distribution:

| | | |
|---|---|---|
| Ethyl cis-2,2-dimethyl-3-(2,2,2-trichloro-ethyl(cyclopropane-1-carboxylate (cis-Compound Z) | 9.2% | |
| Ethyl trans-2,2-dimethyl-3-(2,2,2-trichloroethyl)cyclopropane-1-carboxylate (trans-Compound Z) | 65.1% | C/T = 12/88* |
| Ethyl trans-3-(2,2-dichloroethenyl)-2,2-dimethylcyclopropane-1-carboxylate (trans-Compound C) | 5.0% | |
| Starting material (compound B) | 13.8% | |
| Others | 6.9% | |
| (b) Compound B | Same as in (a) | |
| Scale | Same as in (a) | |
| Base | Same as in (a) | |
| Solvent | Same as in (a) | |
| Cosolvent | hexamethylphosphoramide | |
| Ratio Solvent/Cosolvent | 5/1 by volume | |
| Procedure | | |

*C/T means cis/trans ratio.

Sodium tert-butoxide (0.5 g, 5.2 mmol) was added over 40 minutes to ethyl 4,6,6,6-tetrachloro-3,3-dimethylhexanoate (1.55 g, 5 mmol) in 1 ml of hexamethylphosphoramide and 5 ml of n-hexane at −26° C. After 2 hours an additional 0.1 g of sodium tert-butoxide was added and the mixture was stirred for 2 more hours at −26° C., then stored at about −70° C. overnight. An additional 0.1 g of sodium tert-butoxide was added at −26° followed after 6½ hours with a further addition of 0.2 g. The reaction was stirred at −26° for an additional 2 hours. The total amount of base added was 0.9 g (9.4 mmol). Analysis of the reaction by glpc showed the following distribution:

| | | |
|---|---|---|
| cis-Compound Z | 53.0% | C/T = 74/26 |
| trans-Compound Z | 18.8% | |
| cis-Compound C | 1.1% | |
| trans-Compound C | 4.6% | |
| Compound B | 15.5% | |
| Others | 7.0% | |

EXAMPLE II

| (a) | Compound B | Ethyl 4,6,6,6-tetrachloro-3,3-dimethyl-hexanoate |
|---|---|---|
| | Scale | 5 mmol |
| | Base | Sodium tert-butoxide (6 mmol) |
| | Solvent | Toluene |
| | Cosolvent | None |
| | Procedure | |

Sodium tert-butoxide (0.58 g, 6 mmol) in 4 ml of toluene was added to ethyl 4,6,6,6-tetrachloro-3,3-dimethylhexanoate (1.55 g, 5 mmol) in 2 ml of toluene. The reaction was conducted at −10° to −5° C. for 2 hours, then at room temperature for 25 hours. Analysis of the reaction mixture by glpc (area percent) showed the following distribution:

| | | |
|---|---|---|
| Ethyl cis-2,2-dimethyl-3-(2,2,2-trichloro-ethyl)cyclopropane-1-carboxylate (cis-Compound Z) | 1.9% | |
| Ethyl trans-2,2-dimethyl-3-(2,2,2-trichloroethyl)cyclopropane-1-carboxylate (trans-Compound Z) | 36.5% | C/T = 5/95 |
| Ethyl trans-3-(2,2-dichloroethenyl)-2,2-dimethylcyclopropane-1-carboxylate (trans-Compound C) | 4.6% | |
| Ethyl 4,6,6-trichloro-3,3-dimethyl-5-hexenoate | 5.3% | |
| Starting material (compound B) | 46.5% | |
| Others | 5.2% | |
| (b) Compound B | Same as in (a) | |
| Scale | Same as in (a) | |
| Base | Same as in (a) | |
| Solvent | Same as in (a) | |
| Cosolvent | Hexamethylphosphoramide | |
| Ratio Solvent/Cosolvent | 12/1 by volume | |
| Procedure | | |

Sodium tert-butoxide (0.58 g, 6 mmol) in 4 ml of toluene was added to ethyl 4,6,6,6-tetrachloro-3,3-dimethylhexanoate (1.55 g, 5 mmol) in 2 ml of toluene and 0.5 ml of hexamethylphosphoramide. The reaction was conducted at −10° to −5° C. for 4½ hours, then at room temperature for 13 hours. Analysis of the reaction mixture by glpc (area percent) showed the following distribution:

| | | |
|---|---|---|
| cis-Compound Z | 37.9% | C/T = 63/37 |
| trans-Compound Z | 22.4% | |
| cis-Compound C | 0.7% | |
| trans-Compound C | 3.7% | |
| Ethyl 4,6,6-trichloro-3,3-dimethyl- | | |

-continued

| 5-hexenoate | 4.7% |
|---|---|
| Compound B | 29.4% |
| Others | 1.2% |

EXAMPLE III

| (a) Compound B | Ethyl 4,6,6,6-tetrachloro-3,3-dimethyl-hexanoate |
|---|---|
| Scale | 5 mmol |
| Base | Sodium tert-butoxide (9.4 mmol) |
| Solvent | Tetrahydrofuran |
| Cosolvent | None |
| Procedure | |

Sodium tert-butoxide (0.9 g, 9.4 mmol) was added in solid form to ethyl 4,6,6,6-tetrachloro-3,3-dimethylhexanoate (1.55 g, 5 mmol) in 5 ml of tetrahydrofuran. The reaction was conducted at $-26°$ C. for 10 hours. Analysis of the reaction mixture by glpc (area percent) showed the following distribution:

| | | |
|---|---|---|
| Ethyl cis-2,2-dimethyl-3-(2,2,2-trichloroethyl)cyclopropane-1-carboxylate (cis-Compound Z) | 43.4% | |
| Ethyl trans-2,2-dimethyl-3-(2,2,2-trichloroethyl)cyclopropane-1-carboxylate (trans-Compound Z) | 20.6% | C/T = 68/32 |
| Ethyl cis-3-(2,2-dichloroethenyl)-2,2-dimethylcyclopropane-1-carboxylate (cis-Compound C) | 4.5% | |
| Ethyl trans-3-(2,2-dichloroethenyl)-2,2-dimethylcyclopropane-1-carboxylate (trans-Compound C) | 17.4% | |
| Ethyl 3-(chloroethynyl)-2,2-dimethylcyclopropane-1-carboxylate | 1.3% | |
| Ethyl 4,6,6-trichloro-3,3-dimethyl-5-hexenoate | 4.0% | |
| Starting material (compound B) | 5.6% | |
| Others | 3.2% | |
| (b) Compound B | Same as in (a) | |
| Scale | Same as in (a) | |
| Base | Same as in (a) | |
| Solvent | Same as in (a) | |
| Cosolvent | Hexamethylphosphoramide | |
| Ratio Solvent/Cosolvent | 10/1 by volume | |
| Procedure | | |

Sodium tert-butoxide (0.90 g, 9.4 mmol) was added in solid form to ethyl 4,6,6,6-tetrachloro-3,3-dimethylhexanoate (1.55 g, 5 mmol) in 5 ml of tetrahydrofuran and 0.5 ml of hexamethylphosphoramide. The reaction was conducted for 6 hours at $-26°$ C. Analysis of the reaction mixture by glpc (area percent) showed the following distribution:

| | | |
|---|---|---|
| cis-Compound Z | 64.0% | C/T = 79/21 |
| trans-Compound Z | 17.4% | |
| cis-Compound C | 2.9% | |
| trans-Compound C | 9.3% | |
| Ethyl 4,6,6-trichloro-3,3-dimethyl-5-hexenoate | 3.4% | |
| Compound B | 2.3% | |
| Others | 0.7% | |

The following examples further illustrate the conversion of compound B to high cis compound Z by the process of the invention.

EXAMPLE IV

| (a) Compound B | Ethyl 4,6,6,6-tetrachloro-3,3-dimethylhexanoate |
|---|---|
| Scale | 5 mmol |
| Base | Sodium tert-butoxide (7.5 mmol) |
| Solvent | Hexane |
| Cosolvent | Dimethylformamide |
| Ratio Solvent/Cosolvent | 5/1 |
| Procedure | |

Sodium tert-butoxide was added in six 0.12 g portions (a total of 0.72 g, 7.5 mmol) at 10 minute intervals to ethyl 4,6,6,6-tetrachloro-3,3-dimethylhexanoate (1.55 g, 5 mmol) in 5 ml of n-hexane and 1 ml of dimethylformamide at $-40°$ C. The reaction was continued for a total time of 6 hours. Analysis by glpc (area percent) of the reaction mixture showed the following distribution:

| | | |
|---|---|---|
| Ethyl cis-2,2-dimethyl-3-(2,2,2-trichloroethyl)cyclopropane-1-carboxylate (cis-Compound Z) | 55.3% | C/T = 78/22 |
| Ethyl trans-2,2-dimethyl-3-(2,2,2-trichloroethyl)cyclopropane-1-carboxlate (trans-Compound Z) | 15.5% | |
| Ethyl cis-3-(2,2-dichloroethenyl)-2,2-dimethylcyclopropane-1-carboxylate (cis-Compound C) | 0.9% | |
| Ethyl trans-3-(2,2-dichloroethenyl)-2,2-dimethylcyclopropane-1-carboxylate (trans-Compound C) | 5.1% | |
| Ethyl 4,6,6-trichloro-3,3-dimethyl-5-hexenoate | 4.8% | |
| Starting material (compound B) | 17.3% | |
| Others | 1.1% | |

(b) Same as in (a) except the reaction temperature was $-5°$ C. to $0°$ C. Analysis by glpc (area percent) of the reaction mixture showed the following distribution:

| | | |
|---|---|---|
| cis-Compound Z | 45.1% | C/T = 72/28 |
| trans-Compound Z | 17.4% | |
| cis-Compound C | 3.4% | |
| trans-Compound C | 11.4% | |
| Ethyl 4,6,6-trichloro-3,3-dimethyl-5-hexenoate | 10.2% | |
| Compound B | 9.6% | |
| Others | 2.9% | |

EXAMPLE V

| Compound B | Ethyl 4,6,6,6-tetrachloro-3,3-dimethylhexanoate |
|---|---|
| Scale | 5 mmol |
| Base | Sodium tert-butoxide (6.2 mmol) |
| Solvent | Hexane |
| Cosolvent | Dimethylsulfoxide |
| Ratio Solvent/Cosolvent | 10/1 |
| Procedure | |

Sodium tert-butoxide (0.3 g, 3.1 mmol) was added to ethyl 4,6,6,6-tetrachloro-3,3-dimethylhexanoate (1.55 g, 5 mmol) in 5 ml of n-hexane and 1 ml of dimethylsulfoxide at $-26°$ C. After 5 hours at this temperature an additional 0.3 g of sodium tert-butoxide was added and the reaction was continued for two more hours. Analysis of the reaction mixture by glpc (area percent) showed the following distribution:

Ethyl cis-2,2-dimethyl-3-(2,2,2-trichloro-

-continued

| | |
|---|---|
| ethyl)cyclopropane-1-carboxylate (cis-Compound Z) | 44.1% |
| Ethyl trans-2,2-dimethyl-3-(2,2,2-trichloroethyl)cyclopropane-1-carboxylate (trans-Compound Z) | 30.0% |
| Ethyl cis-3-(2,2-dichloroethenyl)-2,2-dimethylcyclopropane-1-carboxylate (cis-Compound C) | 4.0% |
| Ethyl trans-3-(2,2-dichloroethenyl)-2,2-dimethylcyclopropane-1-carboxylate (trans-Compound C) | 13.3% |
| Ethyl 4,6,6-trichloro-3,3-dimethyl-5-hexenoate | 1.3% |
| Ethyl 3-(chloroethynyl)-2,2-dimethylcyclopropane-1-carboxylate | 0.4% |
| Ethyl 6,6,6-trichloro-3,3-dimethyl-4-hexenoate | 0.7% |
| Starting material (compound B) | 4.8% |
| Others | 1.4% |

C/T = 60/40

EXAMPLE VI

| | |
|---|---|
| Compound B | Ethyl 4,6,6,6-tetrachloro-3,3-dimethylhexanoate |
| Scale | 5 mmol |
| Base | Sodium tert-butoxide (7.5 mmol) |
| Solvent | Hexane |
| Cosolvent | N-methylpyrrolidone |
| Ratio Solvent/Cosolvent | 20/1 |
| Procedure | |

Sodium tert-butoxide was added in six 0.12 g portions (a total of 0.72 g, 7.5 mmol) at five minute intervals to ethyl 4,6,6,6-tetrachloro-3,3-dimethylhexanoate (1.55 g, 5 mmol) in 5 ml of n-hexane and 0.25 g (0.24 ml) of N-methylpyrrolidone at 4° to 8° C. The reaction was conducted for a total of 2 hours including addition time. Analysis by glpc (area percent) of the reaction mixture showed the following distribution:

| | |
|---|---|
| Ethyl cis-2,2-dimethyl-3-(2,2,2-trichloroethyl)cyclopropane-1-carboxylate (cis-Compound Z) | 35.2% |
| Ethyl trans-2,2-dimethyl-3-(2,2,2-trichloroethyl-cyclopropane-1-carboxylate (trans-Compound Z) | 31.5% |
| Ethyl cis-3-(2,2-dichloroethenyl)-2,2-dimethylcyclopropane-1-carboxylate (cis-Compound C) | 3.1% |
| Ethyl trans-3-(2,2-dichloroethenyl)-2,2-dimethylcyclopropane-1-carboxylate (trans-Compound C) | 9.9% |
| Ethyl 6,6,6-trichloro-3,3-dimethyl-4-hexenoate | 5.9% |
| Ethyl-4,6,6-trichloro-3,3-dimethyl-5-hexenoate | 1.2% |
| Ethyl 3-(chloroethynyl)-2-dimethylcyclopropane-1-carboxylate | 1.3% |
| Starting material (compound B) | 10.9% |
| Others | 1.0% |

C/T = 53/47

EXAMPLE VII

| | |
|---|---|
| Compound B | Ethyl 4,6,6,6-tetrachloro-3,3-dimethylhexanoate |
| Scale | 5 mmol |
| Base | Sodium tert-pentoxide (7.3 mmol) |
| Solvent | Hexane |
| Cosolvent | Hexamethylphosphoramide |
| Ratio Solvent/Cosolvent | 5/1 |
| Procedure | |

Sodium tert-pentoxide (0.61 g, 5.5 mmol) was added all at once to ethyl 4,6,6,6-tetrachloro-3,3-dimethylhexanoate (1.55 g, 5 mmol) in a mixture of 5 ml of n-hexane and 1 ml of hexamethylphosphoramide at −26°. After 3.5 hours an additional 0.2 g (1.8 mmol) of sodium tert-pentoxide was added and the temperature was maintained at −26° for an additional 2 hours. Analysis of the reaction mixture by glpc (area percent) showed the following distribution:

| | |
|---|---|
| Ethyl cis-2,2-dimethyl-3-(2,2,2-trichloroethyl)cyclopropane-1-carboxylate (cis-Compound Z) | 47.0% |
| Ethyl trans-2,2-dimethyl-3-(2,2,2-trichloroethyl)cyclopropane-1-carboxylate (trans-Compound Z) | 16.9% |
| Ethyl cis-3-(2,2-dichloroethenyl)-2,2-dimethylcyclopropane-1-carboxylate (cis-Compound C) | 4.1% |
| Ethyl trans-3-(2,2-dichloroethenyl)-2,2-dimethylcyclopropane-1-carboxylate (trans-Compound C) | 15.6% |
| Ethyl 4,6,6-trichloro-3,3-dimethyl-5-hexenoate | 9.4% |
| Starting material (compound B) | 3.0% |
| Others | 4.0% |

C/T = 74/26

EXAMPLE VIII

| | |
|---|---|
| Compound B | Ethyl 4,6,6,6-tetrachloro-3,3-dimethylhexanoate |
| Scale | 5 mmol |
| Base | Potassium tert-butoxide (7.0 mmol) |
| Solvent | Hexane |
| Cosolvent | Hexamethylphoshoramide |
| Ratio Solvent/Cosolvent | 5/1 |
| Procedure | |

Potassium tert-butoxide (0.68 g, 6.1 mmol) was added all at once to ethyl 4,6,6,6-tetrachloro-3,3-dimethylhexanoate (1.55 g, 5 mmol) in a mixture of 5 ml of n-hexane and 1 ml of hexamethylphosphoramide at −40°. After 3 hours an additional 0.1 g (0.9 mmol) of potassium tert-butoxide was added and the temperature was maintained at −40° for an additional 1 hour. Analysis of the reaction mixture by glpc (area percent) showed the following distribution:

| | |
|---|---|
| Ethyl cis-2,2-dimethyl-3-(2,2,2-trichloroethyl)cyclopropane-1-carboxylate cis-Compound Z) | 66.3% |
| Ethyl trans-2,2-dimethyl-3-(2,2,2-trichloroethyl)cyclopropane-1-carboxylate (trans-Compound Z) | 15.7% |
| Ethyl cis-3-(2,2-dichloroethenyl)-2,2-dimethylcyclopropane-1-carboxylate (cis-Compound C) | 6.3% |
| Ethyl trans-3-(2,2-dichloroethenyl)-2,2-dimethylcyclopropane-1-carboxylate (trans-Compound C) | 11.0% |
| Ethyl 3-chloroethynyl-2,2-dimethylcyclopropane-1-carboxylate | 0.3% |
| Starting material (compound B) | 0% |
| Others | 0.4% |

C/T = 81/19

EXAMPLE IX

| | |
|---|---|
| Compound B | Methyl 4,6,6,6-tetrachloro-3,3-dimethylhexanoate |
| Scale | 0.1 mol |

| | -continued |
|---|---|
| Base | Sodium tert-butoxide (0.11 mol) |
| Solvent | tert-Butanol/hexane |
| Cosolvent | Dimethylacetamide |
| Ratio Solvent/Cosolvent | 6/1 |
| Procedure | Inverse addition |

A 50% dispersion of sodium hydride in mineral oil (5.28 g, 0.11 mol) was washed twice with n-hexane under an argon atmosphere to remove the oil. A mixture of 20 ml of n-hexane and 20 ml of dimethylacetamide was added. To the resulting suspension was added dropwise 100 ml of tert-butanol with water cooling. After stirring for 1 hour at room temperature, a solution of 29.6 g (0.1 mol) of methyl 4,6,6,6-tetrachloro-3,3-dimethylhexanoate in 15.54 g of tert-butanol was added dropwise over a period of 40 minutes while maintaining the temperature at less than $-5°$ C. Stirring was continued at this temperature for an additional 30 minutes, then the mixture was poured into 50 ml of a saturated aqueous ammonium chloride solution and extracted with 200 ml of ether. The ether extracts were combined, washed with brine, dried over magnesium sulfate, and concentrated to give, after distillation, 23.29 g (89.7% yield) of methyl 2,2-dimethyl-3-(2,2,2-trichloroethyl)cyclopropane-1-carboxylate (compound Z), bp 73°–74.5° C./0.3–0.5 mm Hg, purity 94.1%, C/T=77/23. Methyl 3-(2,2-dichloroethenyl)-2,2-dimethylcyclopropane-1-carboxylate (compound C), C/T=27/73, comprised 4.7% of the product.

The following examples illustrate the conversion of high cis compound Z to high cis compound C.

EXAMPLE X

A solution of 23.29 g (0.09 mol) of methyl 2,2-dimethyl-3-(2,2,2-trichloroethyl)cyclopropane-1-carboxylate (C/T=77/23) in 20 ml of n-hexane was added dropwise to 5.4 g (0.1 mol) of sodium methoxide in 80 ml of n-hexane and 20 ml of dimethylacetamide at room temperature. The mixture was stirred for five hours, poured into aqueous ammonium chloride, and extracted with ether. The ether extracts were combined, dried over magnesium sulfate, and concentrated to give, after distillation, 16.30 g (81.5% yield) of methyl 3-(2,2-dichloroethenyl)-2,2-dimethylcyclopropane-1-carboxylate (compound C), bp 59° C./0.3 mm Hg, purity 91.3%, C/T=81/19.

EXAMPLE XI

Hexamethylphosphoramide (10 ml) and 50 ml of n-hexane were added to 0.0604 mol of sodium methoxide, freshly prepared from sodium hydride and methanol. Methyl 2,2-dimethyl-3-(2,2,2-trichloroethyl)cyclopropane-1-carboxylate (compound Z, C/T=75/25, 13 g, 0.050 mol) was added and the mixture was stirred at room temperature for 3 hours. Analysis by glpc of the reaction mixture showed that methyl 3-(2,2-dichloroethenyl)-2,2-dimethylcyclopropane-1-carboxylate, compound C, was formed in 94.2% unisolated yield, C/T=76/24.

EXAMPLE XII

Powdered sodium methoxide was prepared from 2.90 g (0.121 mol) of sodium hydride and 10 ml of methanol. To this dry base were added, in order, 50 ml of n-octane, 13.0 g (0.05 mol) of methyl 2,2-dimethyl-3-(2,2,2-trichloroethyl)cyclopropane-1-carboxylate (compound Z, C/T=77/23), and 10 ml of dimethylacetamide. The reaction was conducted without external temperature control at 100 mm Hg for 2–5 hours. Analysis by glpc indicated 73.8% cis and 13.9% trans for overall product mixture, C/T=82/18 as to methyl 3-(2,2-dichloroethenyl)-2,2-dimethylcyclopropane-1-carboxylate, compound C.

EXAMPLE XIII

A mixture of 13.0 g (0.050 mol) of methyl 2,2-dimethyl-3-(2,2,2-trichloroethyl)cyclopropane-1-carboxylate (compound Z, C/T=77/23), 9.12 g (0.060 mol) of 1,5-diazabicyclo[5.4.0]undec-5-ene and 50 ml of dimethylformamide was stirred at 100° for 1 hour, then allowed to cool to room temperature and poured into 1 N hydrochloric acid. The mixture was extracted with ether and the ether extracts were combined, washed with brine, dried over magnesium sulfate and concentrated to give 10.15 g (91% yield) of methyl 3-(2,2-dichloroethenyl)-2,2-dimethylcyclopropane-1-carboxylate, 94% purity, C/T=76/24.

EXAMPLE XIV

A mixture of 2.6 g (0.01 mol) of methyl 2,2-dimethyl-3-(2,2,2-trichloroethyl)cyclopropane-1-carboxylate (compound Z, C/T=80/20), 1.0 ml of pyrrolidine, and 20 ml of dimethylformamide was heated at 100° for 20 hours to give, by glpc analysis, 68.5% cis and 24.0% trans (C/T=74/26) methyl 3-(2,2-dichloroethenyl)-2,2-dimethylcyclopropane-1-carboxylate, compound C.

The following examples illustrate the use of an alkali metal hydroxide in the conversion of high cis compound Z to the acid of high cis compound C.

EXAMPLE XV

To 10 ml of a 20% aqueous solution of sodium hydroxide (0.05 mole) was added 3.0 g (0.012 mole) of methyl 2,2-dimethyl-3-(2,2,2-trichloroethyl)cyclopropane-1-carboxylate (compound Z, C/T=75/25) and the mixture was heated, gradually over several hours, to 100°. Heating was continued at 100° for a total reaction time of 25 hours during which period aliquots were periodically taken and were poured into aqueous ammonium chloride solution, extracted with ether, and treated with diazomethane in ether to convert the acid produced to the methyl ester for glpc analysis. The reaction mixture was cooled, washed with ether, and the aqueous phase made acidic by the addition of concentrated hydrochloric acid. The acidic mixture was then extracted with ether, and the ether extracts were combined, washed with brine, dried over magnesium sulfate and concentrated to give 1.80 g (74% yield) of methyl 3-(2,2-dichloroethenyl)-2,2-dimethylcyclopropane-1-carboxylic acid, the acid corresponding to compound C, C/T=88/12. By monitoring the reaction it was determined that the reaction was essentially complete in 5 to 6 hours.

EXAMPLE XVI

A mixture of 9.0 g (0.035 mole) of methyl 2,2-dimethyl-3-(2,2,2-trichloroethyl)cyclopropane-1-carboxylate (compound Z, C/T=75/25) in 30 ml of a 20% aqueous solution of sodium hydroxide (0.15 mole) and 10 ml of methanol was heated to 98° over 30 minutes. Heating was continued at this temperature for 5 hours. The reaction mixture was cooled, washed with ether, and the aqueous phase made acidic by the addition of concentrated hydrochloric acid. The acidic mixture was extracted with ether, and the ether extracts were combined, washed with brine, dried over magnesium sulfate, and concentrated to give, after distillation, 5.68 g (78% yield) of methyl 3-(2,2-dichloroethenyl)-2,2-dimethylcyclopropane-1-carboxylic acid, the acid corresponding to compound C, 95% purity, C/T=78/22.

The following examples illustrate the conversion of compound B to high cis compound C without isolation of the intermediate, high cis compound Z.

EXAMPLE XVII

Phase (a): Preparation of high cis methyl 2,2-dimethyl-3-(2,2,2-trichloroethyl)cyclopropane-1-carboxylate (compound Z).

Solid sodium tert-butoxide (0.26 mol) was prepared by adding 38.48 g of tert-butanol in 200 ml of benzene to 6.24 g (0.26 mol) of sodium hydride (freshly prepared from 12.48 g of a 50% dispersion in mineral oil by washing with hexane), stirring for 5 hours at room temperature, and removing the solvent under reduced pressure.

A solution of 29.6 g (0.1 mol) of methyl 4,6,6,6-tetrachloro-3,3-dimethylhexanoate in a mixture of 100 ml of tert-butanol, 20 ml of n-hexane, and 20 ml of dimethylacetamide was cooled to −4° to −6° and the sodium tertbutoxide prepared above was added portionwise over 1.5 hours while maintaining the temperature below −4°. The mixture was stirred for an additional 1.5 hours at ice bath temperature.

Phase (b): Conversion to high cis methyl 3-(2,2-dichloroethenyl)-2,2-dimethylcyclopropane-1-carboxylate (compound C).

Methanol (5 ml) was added to the mixture above and the cooling bath was removed. The mixture was stirred overnight (about 16 hours) at room temperature, then poured into an aqueous ammonium chloride solution and extracted with ether. The ether extracts were combined, washed with brine, dried over magnesium sulfate and concentrated under reduced pressure. The residue was distilled to give 12.90 g 58% yield) of methyl 3-(2,2-dichloroethenyl)-2,2-dimethylcyclopropane-1-carboxylate, compound C, bp 66.5°–68°/0.15–0.2 mm Hg, purity 91%, CT=79/21.

EXAMPLE XVIII

Phase (a): Preparation of high cis methyl 2,2-dimethyl-3-(2,2,2-trichloroethyl)cyclopropane-1-carboxylate (Compound Z).

tert-Butanol (100 ml) was added dropwise below 30° C. to a suspension of 2.91 g (0.11 mol) of sodium hydride (5.82 g of a 50% dispersion of mineral oil) in a mixture of 20 ml of dimethylacetamide and 20 ml of n-hexane. The paste-like mass was stirred for an additional 20 minutes then cooled to −5° C. Methyl 4,6,6,6-tetrachloro-3,3-dimethylhexanoate (29.6 g, 0.10 mol) was added dropwise with vigorous stirring at a rate sufficiently slow to maintain an internal temperature of −6° C.±2°. The resulting solution was stirred for an additional 1 hour with ice-salt cooling.

Phase (b): Conversion to high cis methyl 3-(2,2-dichloroethenyl)-2,2-dimethylcyclopropane-1-carboxylate (compound C).

n-Octane (100 ml) was added to the mixture above and the whole was heated at 40° at 100 mm Hg. A solution of sodium methoxide, prepared from 2.3 g (0.1 mol) of sodium and 60 ml of methanol, was added dropwise and the temperature was maintained at 40° C. at 100 mm Hg for an additional 2 hours during which the methanol was allowed to distill as an azeotrope with octane. The reaction mixture was poured into a saturated aqueous ammonium chloride solution and extracted with ether. The ether extracts were combined, washed with brine, dried over magnesium sulfate, and concentrated to give, after distillation, 15.21 g (68% yield) of methyl 3-(2,2-dichloroethenyl)-3,3-dimethylcyclopropane-1-carboxylate, bp 61°–65° C./0.6 mm Hg, purity 89%, C/T=74/26.

EXAMPLE XIX

Phase (a): Preparation of high cis methyl 2,2-dimethyl-3-(2,2,2-trichloroethyl)cyclopropane-1-carboxylate (Compound Z).

Methyl 4,6,6,6-tetrachloro-3,3-dimethylhexanoate (29.6 g, 0.10 mol) was allowed to react with 0.11 mol of sodium tert-butoxide by the procedure of Example XVIII, Phase (a). Analysis (glpc) of the reaction mixture containing the product showed 95.3% conversion to compound Z, C/T=76/24.

Phase (b): Conversion to high cis methyl 3-(2,2-dichloroethenyl)-2,2-dimethylcyclopropane-1-carboxylate (compound C).

Dimethylformamide (100 ml) and 16.7 g (0.11 mol) of 1,5-diazabicyclo[5.4.0]undec-5-ene (DBU) was added to the reaction mixture above and the whole was heated at 100° with vigorous stirring for 1.5 hours. The mixture was allowed to cool to room temperature then was poured into IN hydrochloric acid and extracted with ether. The ether extracts were combined and washed with aqueous sodium bicarbonate solution, then dried over magnesium sulfate and concentrated to give, after distillation, 17.56 g (79% yield) of methyl 3-(2,2-dichloroethenyl)-2,2-dimethylcyclopropane-1-carboxylate, bp 58°–63°/0.5 mm Hg, purity 99.6%, C/T=76/24.

The following example illustrates the conversion of compound B to the acid of high cis compound C without isolation of the intermediate, high cis compound Z.

EXAMPLE XX

Phase (a): Preparation of high cis methyl 2,2-dimethyl-3-(2,2,2-trichloroethyl)cyclopropane-1-carboxylate (compound Z).

Methyl 4,6,6,6-tetrachloro-3,3-dimethylhexanoate (29.6 g, 0.10 mol) was allowed to react with 0.11 mol of sodium tert-butoxide by the procedure of Example XVIII, Phase (a). Analysis (glpc) of the reaction mixture containing the product showed 95.5% conversion to compound Z, C/T=73/27.

Phase (b): Conversion to high cis 3-(2,2-dichloroethenyl)-2,2-dimethylcyclopropane-1-carboxylic acid (compound C acid). Sodium hydroxide (20 g, 0.5 mole) in 100 ml of water was added to the reaction mixture above with vigorous stirring and the whole was heated at 100° for 5 hours under conditions allowing for the distillation of the tert-butanol present from the Phase (a) reaction. The mixture was allowed to cool to room temperature, then washed with ether and made acidic with concentrated hydrochloric acid. The acidified mixture was extracted with ether and the ether extracts were combined, washed with brine, dried over magnesium sulfate and concentrated to give, after distillation, 18.22 g (87% yield) of 3-(2,2-dichloroethenyl)-2,2-dimethylcyclopropane-1-carboxylic acid, bp 102°–105°/0.3 mm Hg, purity 97.3%, C/T=78/22.

It is apparent that examples of the process of this invention may be multiplied indefinitely without departing from the scope of the invention as defined in the following claims.

We claim:

1. A process for preparing a cis rich compound of the formula Z

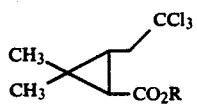 (Z)

wherein R is lower alkyl or a group $R^1$ which is allethrolonyl, tetraphthalimidomethyl, or is represented by the formula

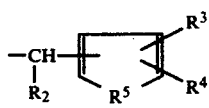

wherein $R^2$ is hydrogen, lower alkyl, lower alkynyl, trihalomethyl, or cyano, $R^3$ and $R^4$ are independently hydrogen, lower alkyl, lower alkenyl, benzyl, phenylthio or are joined to form a methylenedioxy group attached to two adjacent ring carbon atoms of a benzene ring, and $R^5$ is divalent oxygen or sulfur or vinylene, which comprises contacting a compound of the formula B

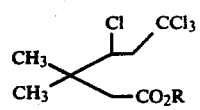 (B)

wherein R is as defined above with 1 to 3 moles per mole of B of an alkali metal tertiary alkoxide of 4 to 6 carbon atoms at a temperature of about −80° C. to about 30° C. in the presence of a solvent system comprising
  (a) a solvent selected from
    (1) an aliphatic hydrocarbon of 5 to 8 carbon atoms,
    (2) an aromatic hydrocarbon having 6 ring carbon atoms, optionally substituted with 1 to 3 substituents selected from alkyl of 1 or 2 carbon atoms and chlorine,
    (3) A tertiary alcohol of 4 to 6 carbon atoms,
    (4) an ether selected from diethyl ether, 1,2-dimethoxyethane, 2-methoxyethyl ether, tetrahydrofuran, and dioxane, and
    (5) a mixture of any of the above solvents, and
  (b) a dipolar aprotic cosolvent selected from
    (1) hexamethylphosphoramide,
    (2) dimethylformamide,
    (3) dimethylacetamide,
    (4) dimethylsulfoxide, and
    (5) N-methylpyrrolidone,
the ratio of solvent to cosolvent being in the range of 20:1 to 2:1 by volume.

2. The process of claim 1 wherein R is lower alkyl.

3. The process of claim 1 wherein R is 3-phenoxybenzyl, α-cyano-3-phenoxybenzyl, or 5-benzyl-3-furylmethyl.

4. The process of claim 1 conducted at a temperature of from −60° C. to −10° C.

5. The process of claim 1 conducted at a temperature of from −25° C. to 10° C.

6. The process of claim 1 in which the solvent is hexane, toluene, tertiary butyl alcohol, or tetrahydrofuran, or a mixture thereof, and the cosolvent is hexamethylphosphoramide, dimethylformamide, or dimethylacetamide.

7. The process of claim 1 in which the ratio of solvent to cosolvent is from 3:1 to 10:1 by volume respectively.

* * * * *

UNITED STATES PATENT AND TRADEMARK OFFICE
CERTIFICATE OF CORRECTION

PATENT NO. : 4,166,064
DATED : August 28, 1979
INVENTOR(S) : Kiyoshi Kondo; Akira Negishi; Kikuo Sugimoto It is certified that error appears in the above-identified patent and that said Letters Patent are hereby corrected as shown below:

Column 11, EXAMPLE VI, 2nd table, 17th line, "Ethyl 3-chloroethynyl-2-dimethylcyclo-" should read --Ethyl 3-chloroethynyl-2,2-dimethylcyclo- --. Column 12, 1st table, 14th line, "hexanoate" should read --hexenoate--.

Signed and Sealed this

Seventeenth Day of June 1980

[SEAL]

Attest:

SIDNEY A. DIAMOND

*Attesting Officer*   *Commissioner of Patents and Trademarks*